US012601664B2

(12) United States Patent
Kim et al.

(10) Patent No.: US 12,601,664 B2
(45) Date of Patent: Apr. 14, 2026

(54) LOW-CONCENTRATION AIR POLLUTANT SELECTIVE DETECTION DEVICE

(71) Applicant: KOREA RESEARCH INSTITUTE OF CHEMICAL TECHNOLOGY, Daejeon (KR)

(72) Inventors: Sangjoon Kim, Daejeon (KR); Iljeong Heo, Daejeon (KR); Jin Hee Lee, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 291 days.

(21) Appl. No.: 18/272,417

(22) PCT Filed: Jan. 14, 2022

(86) PCT No.: PCT/KR2022/000754
§ 371 (c)(1),
(2) Date: Jul. 14, 2023

(87) PCT Pub. No.: WO2022/154587
PCT Pub. Date: Jul. 21, 2022

(65) Prior Publication Data
US 2024/0077390 A1     Mar. 7, 2024

(30) Foreign Application Priority Data
Jan. 15, 2021    (KR) ........................ 10-2021-0006060

(51) Int. Cl.
*G01N 1/40*        (2006.01)
*G01N 1/22*        (2006.01)
(Continued)

(52) U.S. Cl.
CPC ......... *G01N 1/405* (2013.01); *G01N 33/0011* (2013.01); *G01N 1/2202* (2013.01);
(Continued)

(58) Field of Classification Search
CPC ............... G01N 1/405; G01N 33/0011; G01N 33/0019; G01N 2001/2223; G01N 1/24;
(Continued)

(56) References Cited

U.S. PATENT DOCUMENTS

| | | | |
|---|---|---|---|
| 6,393,894 B1 * | 5/2002 | Bonne ..................... | G01N 1/40 |
| | | | 73/31.07 |
| 2022/0266192 A1 * | 8/2022 | Heo ......................... | G01N 1/22 |
| 2024/0077390 A1 * | 3/2024 | Kim ..................... | G01N 1/2214 |

FOREIGN PATENT DOCUMENTS

| | | | | |
|---|---|---|---|---|
| EP | 1046422 A2 * | 10/2000 | ............. | B01D 53/02 |
| EP | 1413348 A1 * | 4/2004 | ............. | B01J 20/12 |

(Continued)

OTHER PUBLICATIONS

Ao et al., nhancement effect of TiO2 immobilized on activated carbon filter for the photodegradation of pollutants at typical indoor air level, pplied Catalysis B: Environmental 44 (2003) 191-205 (Year: 2003).*

(Continued)

*Primary Examiner* — Stephanie E Bloss
*Assistant Examiner* — Kevin C Butler
(74) *Attorney, Agent, or Firm* — Hauptman Ham, LLP

(57)        ABSTRACT

The present invention relates to a low-concentration air pollutant selective detection device and, more specifically, to a low-concentration air pollutant selective detection device capable of detecting a low-concentration air pollutant with high sensitivity, and selectively detecting an air pollutant when necessary. The low-concentration air pollutant selective detection device of the present invention comprises: a sensor which is located in a flow path, through which the gas moves, to detect contaminants in the gas; and a concentrator part which, by including an adsorbent that is positioned in the flow path of the gas that moves to the sensor and adsorbs contaminants in the gas, and a desorption means that is (Continued)

positioned adjacent to the adsorbent to individually desorb different contaminants from the adsorbent, delivers the concentrated contaminants to the sensor.

11 Claims, 7 Drawing Sheets

(51) Int. Cl.
*G01N 1/24* (2006.01)
*G01N 33/00* (2006.01)

(52) U.S. Cl.
CPC ......... *G01N 1/2205* (2013.01); *G01N 1/2208* (2013.01); *G01N 2001/2223* (2013.01); *G01N 1/24* (2013.01); *G01N 33/0019* (2024.05)

(58) Field of Classification Search
CPC ... G01N 1/2202; G01N 1/2205; G01N 1/2208
USPC ........................................................ 73/28.04
See application file for complete search history.

(56) References Cited

FOREIGN PATENT DOCUMENTS

| | | | | | |
|---|---|---|---|---|---|
| JP | H8-101175 | A | | 4/1996 | |
| JP | H08101175 | A | * | 4/1996 | |
| JP | 2003-530539 | A | | 10/2003 | |
| JP | 2009-47593 | A | | 3/2009 | |
| JP | 2009047593 | A | * | 3/2009 | |
| JP | 2009160484 | A | * | 7/2009 | |
| JP | 2010032178 | A | * | 2/2010 | |
| JP | 5011026 | B2 | * | 8/2012 | |
| JP | 2013202595 | A | * | 10/2013 | |
| JP | 2015-197400 | A | | 11/2015 | |
| JP | 6334221 | B2 | * | 5/2018 | |
| JP | 2018141800 | A | * | 9/2018 | |
| KR | 20010014626 | A | * | 2/2001 | ............ B01D 53/06 |
| KR | 101634653 | B1 | * | 6/2016 | ............ B01D 53/02 |
| KR | 101971176 | B1 | * | 4/2019 | ............ B01D 47/06 |
| KR | 10-2020-0122743 | A | | 10/2020 | |
| KR | 102255620 | B1 | * | 5/2021 | ........ B01D 53/0438 |
| KR | 102640852 | B1 | * | 2/2024 | ............ F25D 29/00 |
| WO | WO-0076628 | A1 | * | 12/2000 | ........ B01D 53/0476 |
| WO | WO-0107903 | A2 | * | 2/2001 | ............... G01N 1/40 |
| WO | WO-2006074343 | A2 | * | 7/2006 | ............ B01D 53/02 |
| WO | WO-2015151537 | A1 | * | 10/2015 | .......... G01N 1/2214 |

OTHER PUBLICATIONS

Bang et al., A carbon nanotube sponge as an adsorbent for vapor preconcentration of aromatic volatile organic compounds, Journal of Chromatography, https://doi.org/10.1016/j.chroma.2019.460363 0021-9673/ © 2019, pp. 1-9 (Year: 2019).*

International Search Report issued on Apr. 22, 2022, for corresponding International Patent Application No. PCT/KR2022/000754, along with an English translation (6 pages).

Written Opinion issued on Apr. 22, 2022, for corresponding International Patent Application No. PCT/KR2022/000754 (4 pages).

* cited by examiner

FIG. 2

LOW-CONCENTRATION AIR POLLUTANT SELECTIVE DETECTION DEVICE

CROSS-REFERENCE TO RELATED APPLICATION

The present application is a national stage filing under 35 U.S.C § 371 of PCT application number PCT/KR2022/000754 filed on Jan. 14, 2022, which is based upon and claims the benefit of priorities to Korean Patent Application No. 10-2021-0006060 filed on Jan. 15, 2021, in the Korean Intellectual Property Office. All of the aforementioned applications are hereby incorporated by reference in their entireties.

TECHNICAL FIELD

The present invention relates to a low-concentration air pollutant selective detection device and, more specifically, to a low-concentration air pollutant selective detection device capable of detecting a low-concentration air pollutant with high sensitivity, and selectively detecting an air pollutant when necessary.

BACKGROUND ART

Air pollutant means that trace substances that adversely affect organisms or substances are included in the air, and may be divided into gaseous contaminant and dust. The former includes sulfur dioxide and carbon monoxide, and the latter includes trace heavy metals, silicic acid, organic substances, and the like.

When a human body is exposed to high-concentration air pollutant for a long time, various devices have been developed to measure and process the air pollutant as the air pollutant may adversely affect the human body.

However, most conventional popular detection sensors for measuring air pollutant are capable of detecting up to ppm range, and therefore, have difficulty detecting a very small amount of air pollutant below ppm. Accordingly, high-sensitivity air pollutant sensors capable of detecting up to ppb and ppt concentrations have been developed. However, since the air pollutant sensors are expensive, it has been difficult to practically spread the air pollutant sensors and apply the air pollutant sensors to industry.

Korean Patent Publication No. 10-1634653, titled "Adsorbent for Concentration of Gas Analytes and Manufacture Method of The Adsorbent, Detecting Method of Gas Analyte" discloses an adsorbent capable of adsorbing a trace of toxic gas and a method for detecting the trace of toxic gas, but relates to the desorption of toxic substances from which moisture is excluded through an adsorbent that exhibits water repellency and has the disadvantage in that toxic substances to be measured is very limited, and an analysis time is very long as the toxic substance is measured through several steps such as concentration step, recovery step, removal step, and analysis step.

DISCLOSURE

Technical Problem

An object of the present invention is to provide a detection device capable of selectively detecting various types of air pollutants when necessary.

In addition, an object of the present invention is to provide a detection device capable of high-sensitivity sensing of a sensor by concentrating and then desorbing a trace of air pollutant.

Technical Solution

In one general aspect, a low-concentration air pollutant selective detection device includes: a sensor which is located in a flow path, through which the gas moves, to detect contaminants in the gas; and a concentrator part which, by including an adsorbent that is positioned in the flow path of the gas that moves to the sensor and adsorbs contaminants in the gas, and a desorption means that is positioned adjacent to the adsorbent to individually desorb different contaminants from the adsorbent, delivers the concentrated contaminants to the sensor.

The adsorbent may be arranged in plurality, but at least two of the adsorbents may be made of different materials so that different contaminants are adsorbed, and the desorption means may be positioned adjacent to each adsorbent and desorbs the contaminant adsorbed to each adsorbent.

The adsorbent may be a porous adsorption structure and is installed to partition the flow path, and the desorption means may be installed to surround an outer circumferential surface of the adsorbent.

The desorption means may be a heating structure and is installed to partition the flow path, and the adsorbent may include an adsorption material coated on a surface of the heating structure.

The heating structure may be any one metal of iron (Fe), chromium (Cr), aluminum (Al), nickel (Ni), platinum (Pt), molybdenum (Mo), tungsten (W), and tantalum (Ta) or an alloy thereof.

The heating structure may be any one of silicon carbide (SiC)-based, molybdenum silicide (MoSi2)-based, carbon-based, and zirconia-based heating elements.

The adsorption material may be any one or two or more selected from the group consisting of silica gel, activated alumina, synthetic zeolite, charcoal, bone charcoal, activated carbon, metal organic frameworks (MOF), hyper-crosslinked polymeric resin (HPR), and zeolites.

The low-concentration air pollutant selective detection device may further include: a main line which forms a main flow path through which gas introduced from the outside moves to the sensor; the concentrator part which is located in the main flow path; and a subline which is positioned between the concentrator part and the sensor and forms a sub-flow path branched from the main flow path.

The concentrator part may be provided in plurality and may be connected in parallel to each other in the main flow path.

A low-concentration air pollutant selective detection method includes: an adsorption mode including a step of adsorbing different contaminants included in gas to adsorbents of different materials included in a concentrator part, respectively; and a desorption mode including a step of individually detaching different contaminants from the adsorbent and moving the contaminants to a sensor by a desorption means positioned adjacent to the adsorbent, in which the adsorption mode and the desorption mode may be selectively performed.

The adsorption mode may include a step in which a main flow path is opened and gas is introduced into the concentrator part located in the main flow path; a step of adsorbing different contaminants to each adsorbent, and a step in which the gas passing through the adsorbent is discharged through a sub-flow path branched from the main flow path, and the desorption mode may include a step of desorbing the contaminant from the adsorbent by any one or two or more desorption means selected from a desorption means positioned adjacent to each adsorbent, a step of moving the desorbed contaminant to a sensor along the main flow path, and a step of measuring information including a concentration of the contaminant by the sensor.

The desorption mode may proceed when a set period of time elapses in the adsorption mode.

Advantageous Effects

According to a low-concentration air pollutant selective detection device of the present invention, it is possible for a sensor to realize high-sensitivity sensing as a trace of air pollutants are adsorbed and concentrated by a concentrator part equipped with an adsorbent and then desorbed in a large amount.

In addition, by separately desorbing contaminants attached to each adsorbent as needed through a desorption means, it is possible to selectively sense the contaminants.

BRIEF DESCRIPTION OF THE DRAWINGS

FIG. 2 is a partially cut-away perspective view illustrating main parts of the low-concentration air pollutant selective detection device illustrated in FIG. 1.

BEST MODE

Figure 1:
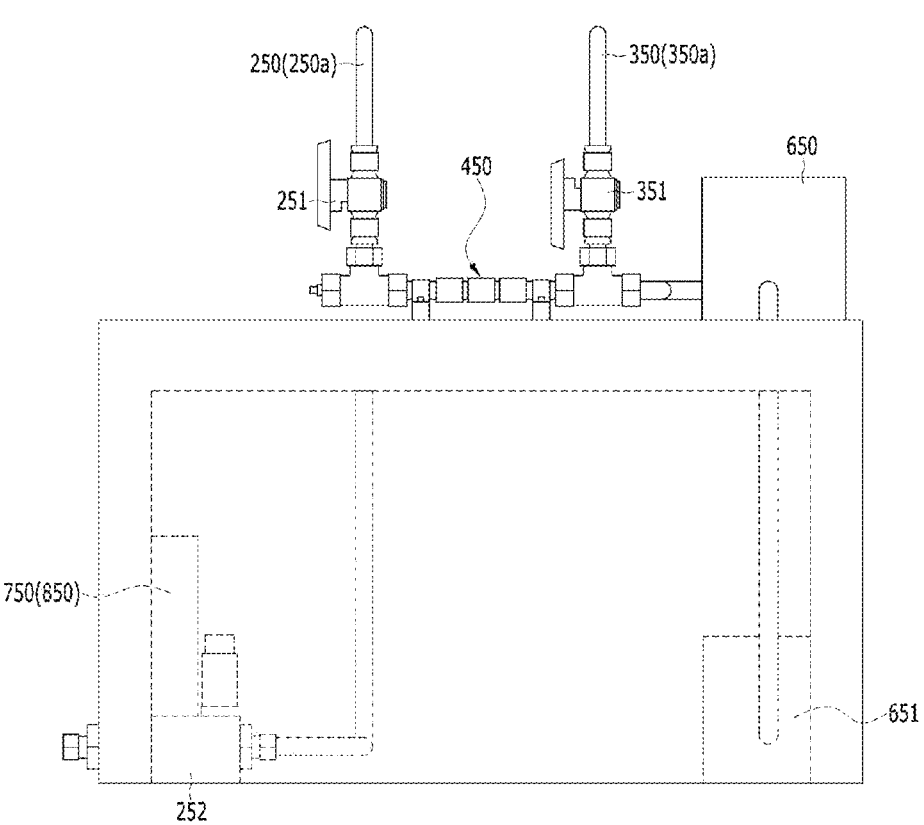
FIG. 1 is a front view of a low-concentration air pollutant selective detection device according to a first embodiment of the present invention.

Technical terms and scientific terms used herein have the general meaning understood by those skilled in the art to which the present invention pertains unless otherwise defined, and a description for the known function and configuration unnecessarily obscuring the gist of the present invention will be omitted in the following description and the accompanying drawings.

Also, the singular forms used in the specification are intended to include the plural forms as well, unless the context specifically dictates otherwise.

In addition, unless specifically stated, units used in this specification are based on weight, and as an example, a unit of % or ratio means weight % or weight ratio, and unless otherwise defined, weight % means wt % means weight % of any one component in the composition out of the total composition.

In addition, numerical ranges as used herein include all possible combinations of lower and upper limits and all values within that range, increments logically derived from the form and width of the defined ranges, all values defined herein, and upper and lower limits of numerical ranges defined in different forms. Unless otherwise defined in the specification of the present invention, values out of a numerical range that may occur due to experimental errors or rounding of values are also included in the defined numerical range.

"Including" mentioned herein is an open-ended description having an equivalent meaning to expressions such as "comprising," "containing," "having," "characterizing," and elements, materials, or processes not listed additionally are not excluded.

A low-concentration air pollutant selective detection device of the present invention includes: a sensor which is located in a flow path, through which the gas moves, to detect contaminants in the gas; and a concentrator part which, by including an adsorbent that is positioned in the flow path of the gas that moves to the sensor and adsorbs contaminants in the gas, and a desorption means that is positioned adjacent to the adsorbent to individually desorb different contaminants from the adsorbent, delivers the concentrated contaminants to the sensor.

Conventionally, an air pollutant detection device has difficulty in measuring a trace of contaminants. Therefore, the contaminant is concentrated in the adsorbent and then desorbed, so the sensing of the sensor is possible through the concentrated contaminant, but as several contaminants move to a sensor unit at the same time, a concentration of a specific contaminant to be sensed is relatively low, so it is difficult to obtain reliable results. In addition, since it is not possible to selectively measure contaminants that need to be measured, it is inconvenient to separately sense each contaminant. In addition, there is a disadvantage in that an analysis time is very long as toxic substances are measured through several steps such as a concentration step, a recovery step, a removal step, and an analysis step.

On the other hand, according to the low-concentration air pollutant selective detection device of the present invention, the high-sensitivity sensing of the sensor is possible as a trace of air pollutant is concentrated by the concentrator part and then delivered to a sensor side. In addition, according to the present invention, the target contaminants may be selectively adsorbed, different contaminants attached to each adsorbent may be individually desorbed through a desorption means when necessary, and then delivered to the sensor. Accordingly, the selective sensing of the contaminant is possible.

Hereinafter, an embodiment of the present invention will be described in detail with reference to the accompanying drawings.

Figure 2:
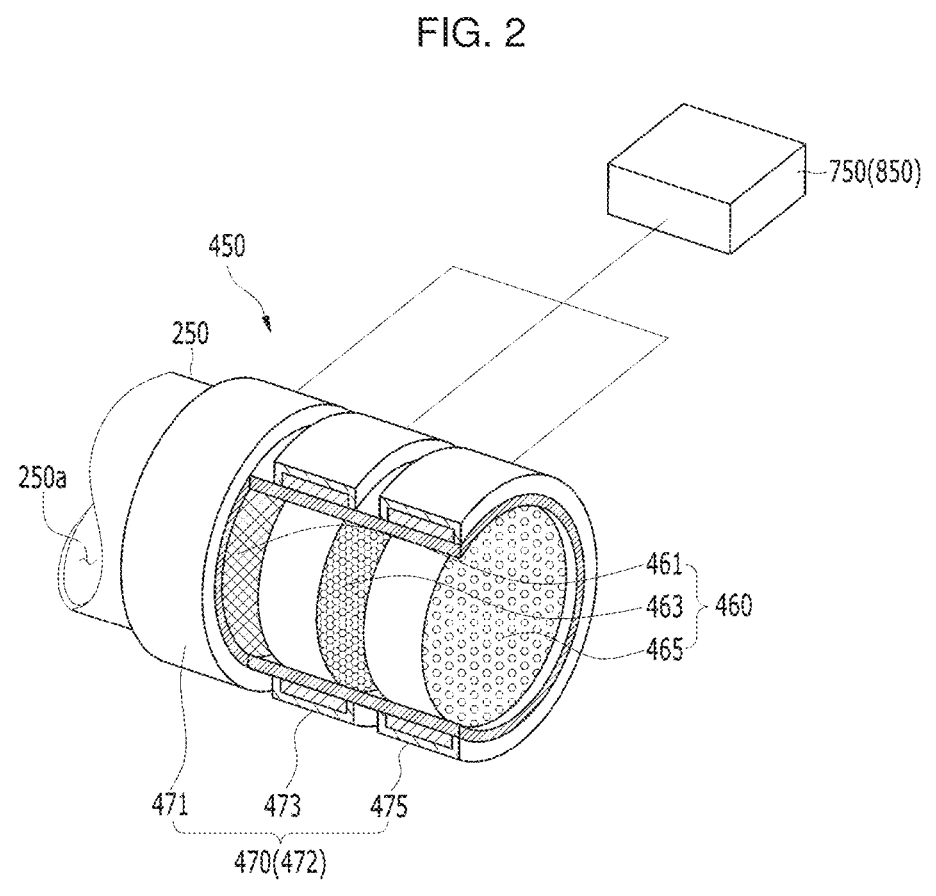

FIGS. 1 and 2 illustrate a low-concentration air pollutant selective detection device according to an embodiment of the present invention.

Referring to FIGS. 1 and 2, the low-concentration air pollutant selective detection device according to the embodiment of the present invention may include a main member 250 which forms a main flow path 250a through which gas introduced from the outside moves to a sensor 650, a concentrator part 450 which is located in the main flow path 250a, and a sub-member 350 which is located between the concentrator part 450 and the sensor 650 and forms a sub-flow path 350a branched from the main flow path 250a.

In detail, the main member 250 forms the main flow path 250a which is a passage through which gas containing a contaminant moves. As illustrated in the drawings, the main member 250 may be provided as a tubular member, but may be a body having an internal space such as an enclosure.

That is, the main member 250 forms the main flow path 250a, which is a passage through which gas moves, and is not limited as long as it has a structure in which the concentrator part 450 may be installed. The main member 250 is opened and closed by a first valve 251 to control whether gas is supplied from the outside. In addition, the main member 250 may be connected to a mass flow controller (MFC) 252. The gas introduced through the main member 250 is a contaminant-containing gaseous phase, and may be, for example, unpurified atmosphere, but is not limited thereto.

Specifically, the sensor 650 may be a known chemical sensor capable of detecting various contaminants. For example, a semiconductor type gas sensor using an oxide semiconductor material, an ionization type gas sensor that detects VOC by making the VOC collide with electrons and ionizing the VOC, or a catalytic combustion type gas sensor using catalysts, such as palladium and platinum, and alumina carrier may be exemplified. As a specific example, the semiconductor gas sensor may be a sensor using metal oxides such as $SnO_2$, $TiO_2$, $ZrO$, and $In_2O_3$, and may be a sensor that measures the concentration and type of gas by using a surface reaction of the sensor generated by adsorption and desorption of ambient gas, but is not limited thereto. Unlike illustrated in the drawings, a plurality of sensors may be provided according to the type and number of contaminants.

The concentrator part 450 of the present invention is to adsorb and concentrate various contaminants and move the contaminants to the sensor, and includes an adsorbent 460 capable of adsorbing the contaminants and a desorption means 470 capable of desorbing the contaminants. The adsorbent 460 may adsorb various contaminants or any one type of contaminants. The desorption means 470 is positioned adjacent to each adsorbent 460 and heats the adsorbents to individually desorb the contaminants from the adsorbent 460. For example, when various contaminants having different desorption temperatures are attached to the adsorbent 450 made of one type of material, the contaminants may be individually desorbed by adjusting the temperature applied to the adsorbent 450 through the desorption means 470.

Unlike this, a plurality of adsorbents are arranged, but at least two or more adsorbents 460 are made of different materials and may adsorb different contaminants. In this case, the desorption means 470 is provided in the same number as the adsorbent and is located adjacent to each adsorbent to desorb the contaminants adsorbed to each adsorbent.

Specifically, when only any one type (hereinafter referred to as first contaminant) of contaminants is to be sensed, by operating the desorption means 470 adjacent to the adsorbent 460 made of a material capable of adsorbing the first contaminant, only the first contaminant may be delivered to the sensor 650 and sensed. In addition, when two or more types of contaminants are sensed, by operating the desorption means 470 adjacent to the two adsorbents 460 to which the two types of contaminants are respectively adsorbed, two types of contaminants may be delivered to the sensor 650 and sensed. As described above, as the concentrator part 450 of the present invention may selectively deliver the concentrated contaminant to the sensor 650, it is possible to improve the selectivity of the sensor 650 in sensing contaminants, and as the contaminants that are desorbed at the same temperature may be separated and desorbed, it is possible to perform the sensing with higher selectivity.

In one embodiment of the present invention, as illustrated in the drawing, the concentrator part 450 partitions the main flow path 250a and may include a plurality of adsorbents 460 installed inside the main member 250. The adsorbent 460 may be provided in a porous adsorption structure in which the adsorbent 460 is in contact with gas to adsorb the contaminants, but is formed with fine pores so that gas may pass through.

Specifically, a specific surface area of the porous adsorption structure may be 500 to 5000 $m^2/g$, and more specifically 1000 to 3000 $m^2/g$, but is not limited thereto. A micropore size in the porous adsorption structure is not limited to meso-pores in the range of 2 to 50 nm or macropores in the range of 50 to 500 nm, but a pore volume is 0.1 to 5 $cm^3/g$ on average and specifically 0.2 to 3 $cm^3/g$. In addition, the adsorption capacity of the porous adsorption structure may be 10 to 2000 mg/g, and specifically, 50 to 1500 mg/g.

As described above, the adsorbent 460 provided in the porous adsorption structure may be arranged in various ways, but may be arranged at equal intervals along the moving direction of the gas in the main flow path 250a. Therefore, when the desorption means 470 to be described later is installed adjacent to each adsorbent 460, it may be easy to design the position of the desorption means 470 so that one desorption means 470 affects only one adsorbent 460.

As described above, at least two or more adsorbents 460 of the concentrator part 450 may be made of different materials, and may adsorb different contaminants. Specifically, in the concentrator part 450 of the present invention, assuming that the adsorbents 460 arranged along the gas movement direction of the main flow path 250a are sequentially first to third adsorbents 461, 463, and 465, the first to third adsorbents 461, 463, and 465 may all be made of different materials, whereas the first and third adsorbents 461 and 465 may be made of the same material, and the second adsorbent 463 may be made of a material different from that of the first and third adsorbents 461 and 465. In such a concentrator part 450, the same type of contaminant may be adsorbed to the adsorbent 460 made of the same material, and a different type of contaminants may be adsorbed to the adsorbent 460 made of a different material.

For example, the first adsorbent 461 may be made of a hydrophilic material capable of advantageously adsorbing moisture, and the second adsorbent 463 may be made of a hydrophobic material capable of advantageously adsorbing organic solvents. Specifically, the first adsorbent 461 may contain any one or two or more materials selected from the group consisting of activated clay, silica gel, activated alumina, and synthetic zeolite, and the second adsorbent 463 may contain any one or two or more materials selected from the group consisting of charcoal, bone charcoal, and activated carbon. The adsorbent 460 of the present invention is not limited thereto, and all the conventional adsorbents 460 capable of adsorbing the contaminants contained in gas may be applied, but at least two of the plurality of adsorbents 460 may be made of a different material from each other and adsorb different contaminants.

The desorption means 470 is located adjacent to each of the plurality of adsorbents 460 to individually desorb the contaminants from the adsorbent 460, and all the conventional desorption means 470 capable of desorbing the adsorbed material from the adsorbent 460 can be applied. For example, the desorption means 470 may be an air supplier capable of detaching the contaminant adsorbed to the adsorbent 460 by supplying the carrier gas, or a vibrating body capable of desorbing the contaminant by vibrating the adsorbent 460. Preferably, the desorption means 470 may be a heating body 472 that heats each adsorbent 460 to desorb the contaminant from the adsorbent 460. As the heating body 472 desorbs the contaminant from the adsorbent 460 through heat supply, the desorption speed of the contaminant is fast. Accordingly, a low-concentration air pollutant enrichment kit of the present invention may enable faster sensing.

As the heating body 472, all of the conventional heating body 472 capable of supplying heat energy to heat the adsorbent 460 can be applied, but preferably, the heating body 472 may be a resistor that generates Joule-heating, and the resistor may easily supply and stop heat energy depending on whether or not power is applied to easily heat each adsorbent 460 individually. As illustrated in the drawings, the heating body 472 is a ring-shaped member having a certain area and may be positioned to surround an outer surface of the main member 250 where each adsorbent is located.

When the number of adsorbents 460 is provided, the same number of heating bodies 472 may be provided. As a specific example, assuming that three adsorbents 460 are provided and that the first to third adsorbents 461, 463, and 465 are sequentially along the moving direction of gas, the heating body 472 may be divided into a first heating body 471 formed to surround the outer surface of the main member 250 where the first adsorbent 461 is located, a second heating body 473 formed to surround the outer surface of the main member 250 where the second adsorbent 463 is located, and a third heating body 475 formed to surround the outer surface of the main member 250 where the third adsorbent 465 is located. As illustrated in the drawings, the shape and structure of the heating body 472 capable of heating each of the plurality of adsorbents 460, such as a spiral heating wire and a linear heating wire, are not limited and may be applied.

The sub-member 350 forms a sub-flow path 350a branched from the main flow path 250a, and allows gas passing through the adsorbent 460 to be discharged to the outside without moving to the sensor 650. As illustrated in the drawings, the sub-member 350 may be provided as a tubular member, but is not limited thereto. The sub-flow path 350a of the sub member 350 may be opened and closed by a second valve 351. When the second valve 351 is opened, the gas passing through the concentrator part 450 may be discharged to the outside through the sub-flow path of the sub-member 350. Unlike this, when the second valve 351 is closed, the gas passing through the concentrator part 450 may move to the sensor 650.

The low-concentration air pollutant selective detection device including the concentrator part 450 may operate by the control unit 750 installed adjacent to the main flow path 250a. In addition, necessary power may be provided by a battery 850 installed adjacent thereto. In the drawings, the control unit 750 and the battery 850 are located inside the same housing, but otherwise, the control unit 750 and the battery 850 may be located in separate bodies.

Figure 3:
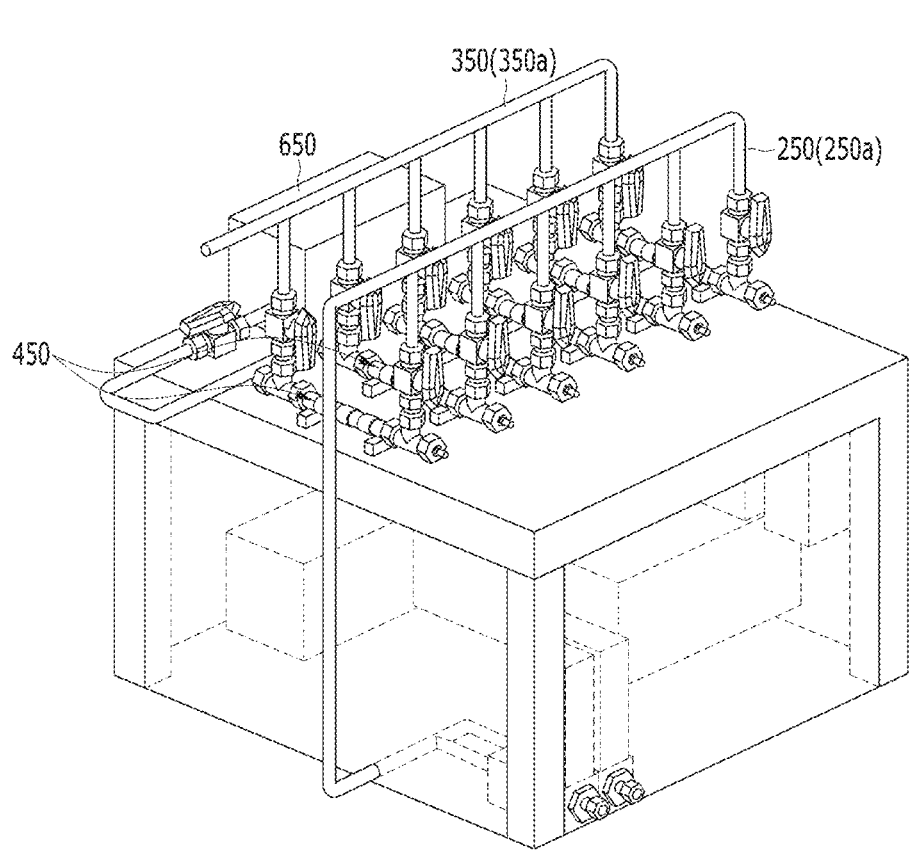
FIG. 3 is a partial cut-away perspective view illustrating main parts of a low-concentration air pollutant selective detection device according to a second embodiment of the present invention.

FIG. 3 illustrates a low-concentration air pollutant selective detection device including a concentrator part according to another embodiment of the present invention.

Referring to FIG. 3, the desorption means of the concentrator part may be provided in a heating structure 570, and the adsorbent may be provided by coating the surface of the heating structure 570 with an adsorbent 571. In such a concentrator part, a contaminant may be adsorbed in proportion to a surface area formed with the heating structure 570 by the adsorption material 571 coated on the surface of the heating structure 570. In addition, when the heating structure 570 generates heat after the contaminant is concentrated in the adsorption material 571, heat energy may be uniformly delivered to the adsorption material 571 coated on the surface of the heating structure 570. Due to this, a large amount of contaminant may be desorbed in a relatively quick time, and the high-sensitivity sensing may be quickly performed.

Specifically, the heating structure 570 is installed to partition the main flow path 250a, and as illustrated in the drawings, a plurality of heating structures 570 may be arranged in a row.

The heating structure is a resistor that generates Joule-heating, and may be any one metal of iron (Fe), chromium (Cr), aluminum (Al), nickel (Ni), platinum (Pt), molybdenum (Mo), tungsten (W), and tantalum (Ta) or an alloy thereof. Alternatively, the heating structure is any one of silicon carbide (SiC)-based, molybdenum silicide ($MoSi_2$)-based, carbon-based, and zirconia-based heating elements, but is not limited thereto. For example, the heating structure may be made of SiC. The form of the heating structure 570 may have a monolith structure including a plurality of channels opened in a direction parallel to the flow path formation direction of the main flow path, and specifically, may be provided in a honeycomb-monolith structure.

Such a heating structure 570 may be arranged in various ways in the main flow path 250a, but as illustrated in the drawings, the heating structure 570 may be spaced apart at equal intervals along the moving direction of the gas in the main flow path 250a. Accordingly, it is possible to prevent mutually adjacent heating structures 570 from interfering with each other.

In this case, the heating structures 570 may each be coated with different adsorption materials. Specifically, assuming that the heating structures 570 arranged along the moving direction of gas of the main flow path 250a are sequentially first to third heating structures 571, 573, and 575, all of the first to third heating structures 571, 573, and 575 may be coated with different adsorption materials. Unlike this, the first and third heating structures 571 and 575 are coated with the same adsorption material, and the second heating structure 573 is coated with an adsorption material different from that of the first and third heating structures 571 and 575. In this way, the same kind of adsorption material 561 may be adsorbed to the heating structure 570 coated with the same adsorption material, and different kinds of contaminants may be adsorbed to the heating structure 570 coated with a different adsorption material 561.

The adsorption material 561 is an adsorbent known in the art, and the usable adsorption material is not limited. For example, the adsorption material may be provided as a hydrophilic material that may advantageously adsorb moisture or a hydrophobic material that may advantageously adsorb organic solvents. Specifically, the adsorption material may contain any one or two or more selected from the group consisting of silica gel, activated alumina, synthetic zeolite, charcoal, bone charcoal, activated carbon, metal organic frameworks (MOF), hypercrosslinked polymeric resin (HPR), and zeolites.

In the low-concentration air pollutant selective detection device having a concentrator part including the heating structure 570 coated with such an adsorption material 561, the heating structure 570 may generate heat by electrical application, and the contaminant adsorbed on the adsorption material 561 coated on the surface of the heating structure may be desorbed.

Figure 4:
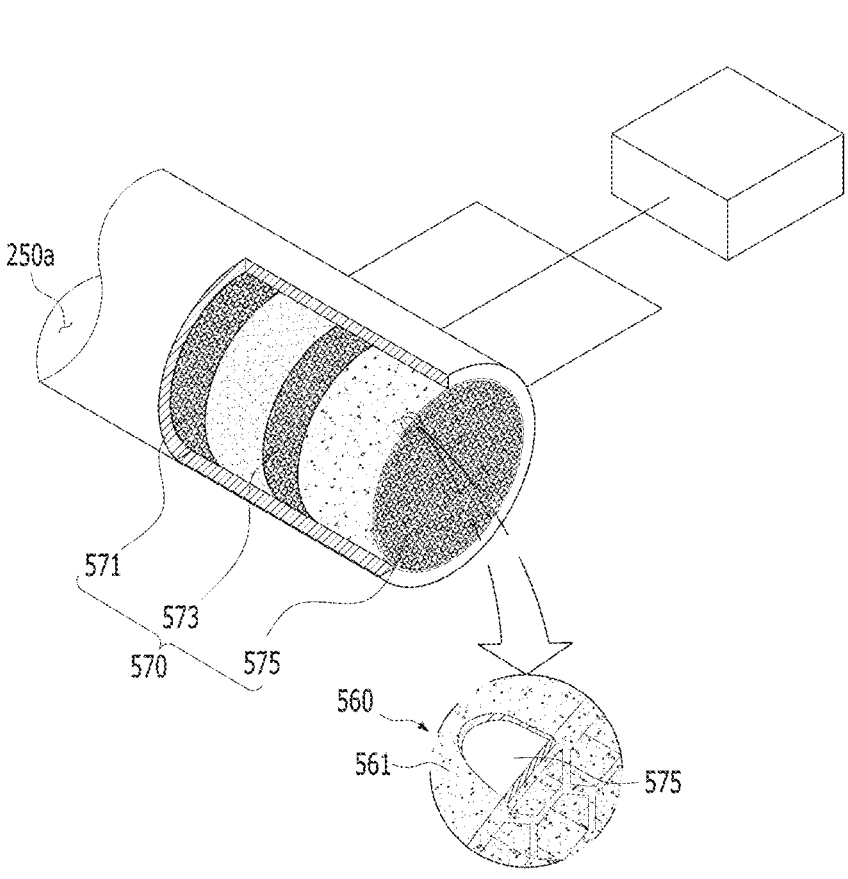
FIG. 4 is a perspective view of a low-concentration air pollutant selective detection device according to a third embodiment of the present invention.

As illustrated in FIG. 4, the low-concentration air pollutant selective detection device of the present invention may include the plurality of concentrator parts 450. In this case, the concentrator part 450 may be connected in parallel to the main flow path 250*a*. In this way, in the low-concentration air pollutant selective detection device, in which the plurality of concentrator parts 450 are connected in parallel to the main flow path 250*a*, various types of adsorbents can be installed, so that more various types of contaminants may be selectively sensed.

The low-concentration air pollutant selective detection device of the present invention described above has excellent sensing sensitivity as the concentrated contaminant is delivered to the sensor, and may selectively sense the required contaminant.

The method of selectively detecting low-concentration air pollutants of the present invention includes: an adsorption mode including a step of adsorbing different contaminants included in gas to adsorbents of different materials included in a concentrator part, respectively; and a desorption mode including a step of individually detaching different contaminants from the adsorbent and moving the contaminants to a sensor by a desorption means positioned adjacent to the adsorbent, in which the adsorption mode and the desorption mode may be selectively performed. Such a detection method may selectively sense the concentrated contaminant for each type when necessary.

Specifically, the adsorption mode includes a step in which a main flow path is opened and gas is introduced into the concentrator part located in the main flow path; a step of adsorbing different contaminants to each adsorbent, and a step in which the gas passing through the adsorbent is discharged through a sub-flow path branched from the main flow path. Such an adsorption mode continuously proceeds for a certain period of time, and the air pollutant may be concentrated in the concentrator part. The execution time of the adsorption mode may proceed without limitation as long as the execution time is a time when the air pollutant may be sufficiently adsorbed to the adsorbent.

The desorption mode may include a step of desorbing the contaminant from the adsorbent by any one or two or more desorption means selected from a desorption means positioned adjacent to each adsorbent, a step of moving the desorbed contaminant to a sensor along the main flow path, and a step of measuring information including a concentration of the contaminant by the sensor. Such an adsorption mode and desorption mode may be selectively performed, but preferably, in the adsorption mode, the desorption mode may proceed after a certain period of time set so that the air pollutant may be sufficiently concentrated.

Hereinafter, the detection method according to the embodiment of the low-concentration air pollutant selective detection device according to the embodiment of the present invention will be described in detail.

In the adsorption mode of the control unit, the first valve 251 installed in the main member 250 is opened, and the outside atmosphere flows in along the main flow path 250*a* and passes through the concentrator part 450 in which the plurality of adsorbents 460 are arranged in a row. In addition, the second valve 351 installed in the sub member 350 is opened, and the gas passing through the concentrator part 450 moves through the sub-flow path 350*a* and is discharged to the outside. The adsorption mode may be maintained for a certain period of time so that the contaminant may be sufficiently adsorbed to the adsorbent 460 of the concentrator part 450.

Thereafter, when a set period of time elapses, the control unit performs the detachment mode. In the desorption mode, the second valve 351 installed in the sub-member 350 is closed, and the heating body 472, which is the desorption means 470, operates to supply heat energy, thereby desorbing the concentrated contaminant from the adsorbent 460. As the second valve 351 is closed, the concentrated contaminant may move to the sensor 650 instead of the sub-member 350, a pump 651 connected to the main flow path 250*a* may be further provided so that the contaminant may easily move to the sensor 650, and the pump 651 operates. In the desorption mode, only one contaminant may be selectively detached by operating only one heating body 472 among the first to third heating bodies 471, 473, and 475 according to the type of contaminant to be sensed. Unlike this, only two heating bodies 472 among the first to third heating bodies 471, 473, and 475 may operate, and all of the first to third heating bodies 471, 473, and 475 may operate.

Hereinafter, the present invention will be described in more detail through Examples. However, the following Inventive Examples are only one reference example for describing the present invention in detail, and the present invention is not limited thereto and may be implemented in various forms.

In addition, unless otherwise defined, all technical and scientific terms have the same meaning as commonly understood by one of ordinary skill in the art to which this invention pertains. The terms used in the description herein are for the purpose of effectively describing particular embodiments only and are not intended to limit the invention.

Example 1

Figure 5:
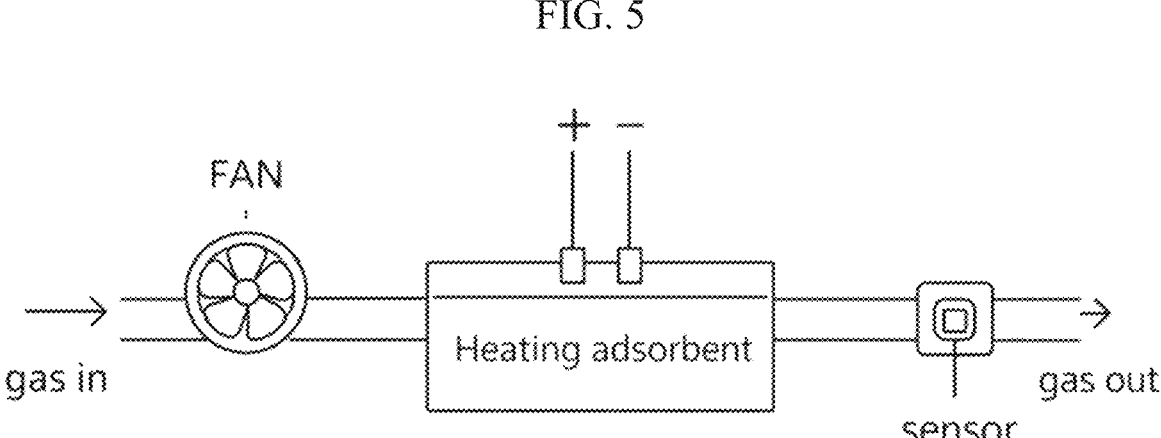
FIG. 5 is a photograph of the low-concentration air pollutant selective detection device according to the embodiment of the present invention.

As illustrated in FIG. 5, after the heating structure with zeolite H-beta (Sigma-Aldrich) coated on the surface thereof was installed in the main flow path of the detection device according to the embodiment of the present invention as the concentrator part, at room temperature, 1 ppm of toluene gas was injected into the main flow path. The toluene gas was supplied through a fan. The heating structure used was made of SiC, and a honeycomb monolith structure was used. The sensor unit used a metal oxide-based electrical resistance change sensor as a commercially available TVOC sensor.

Figure 6:
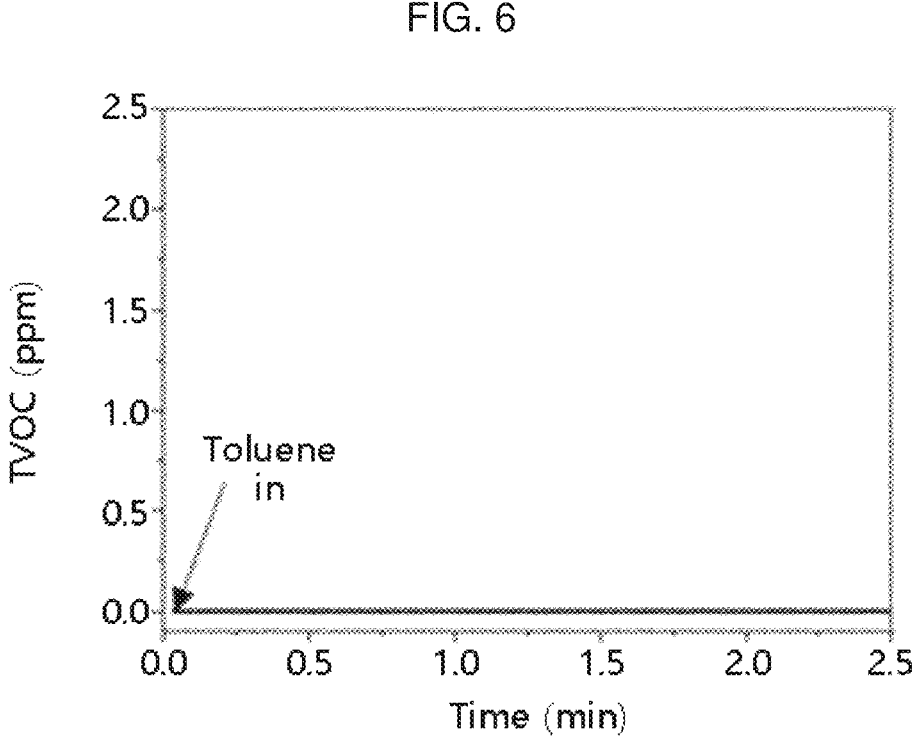
FIGS. 6 and 7 are contaminant detection results through the low-concentration air pollutant selective detection device according to the embodiment of the present invention.
Figure 7:
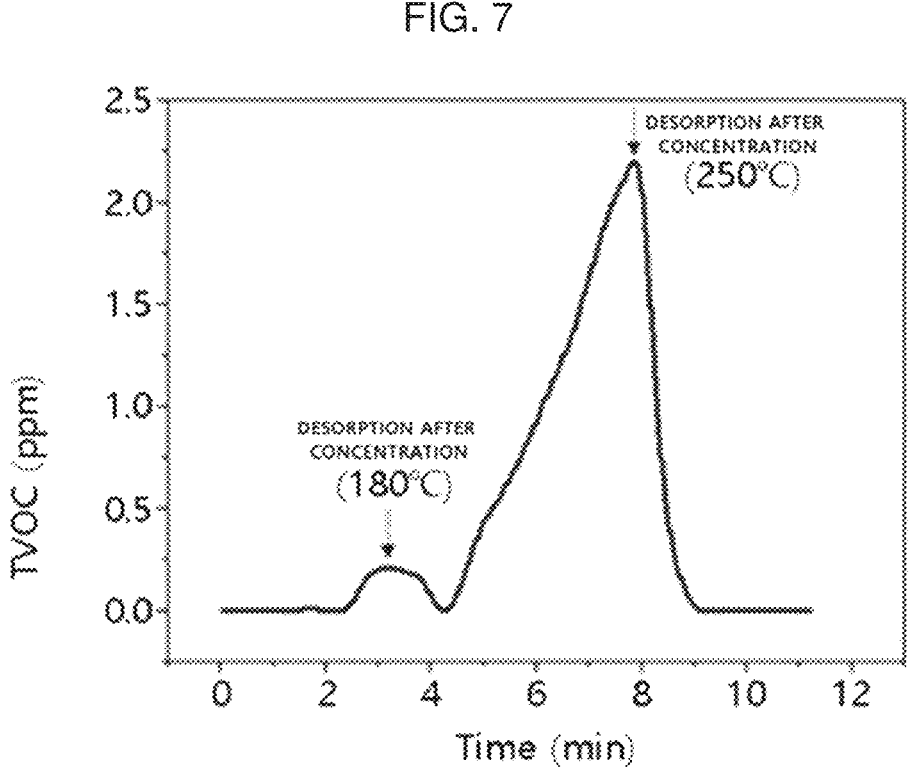

FIGS. 6 and 7 are graphs showing the comparison of the toluene gas sensing values of the detection device according to the presence or absence of the concentrator part of Example 1. Specifically, FIG. 6 is a toluene sensing value of the sensor unit when there is no concentrator part, and FIG. 7 is a toluene sensing value of Example 1. More specifically, after adsorbing and concentrating toluene at room temperature for 15 minutes, a voltage was applied to the heating structure (SiC) to heat the heating structure (SiC), thereby desorbing the concentrated toluene and supplying the concentrated toluene to the sensor unit.

As can be seen in FIG. 7, it was confirmed that the high concentration of toluene was injected into the sensing unit of the sensor due to the desorption of concentrated (adsorbed) toluene when the heating was set to 180° C., and the sensitivity reacted by about 0.2, and when the desorption temperature reached 250° C., the detection more than a sensitivity value of 2 is possible. That is, it was confirmed that the high-sensitivity sensing of the low-concentration air pollutant is possible through the detection device of the present invention.

Hereinabove, although the present invention has been described by specific matters, limited embodiments, and the accompanying drawings, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to these exemplary embodiments, but the claims and all of modifications equal or equivalent to the claims are intended to fall within the scope and spirit of the present invention.

The invention claimed is:

1. A low-concentration air pollutant selective detection device, comprising:
   a sensor located in a flow path, through which gas moves, to detect contaminants in the gas; and
   at least one concentrator part that delivers the contaminants, which are concentrated, to the sensor, the at least one concentrator part including:
      a plurality of adsorbents positioned in the flow path to adsorb the contaminants in the gas, and
      a desorption means positioned adjacent to each of the plurality of adsorbents for desorbing the contaminants from each of the adsorbents,
   wherein
      at least two of the plurality of adsorbents are formed of different materials to adsorb different contaminants, and
      the desorption means desorbs the different contaminants from the at least two adsorbents individually.

2. The low-concentration air pollutant selective detection device of claim 1, wherein each of the adsorbents is a porous adsorption structure and is installed to partition the flow path, and
   the desorption means is installed to surround an outer circumferential surface of each of the adsorbents.

3. The low-concentration air pollutant selective detection device of claim 1, wherein the desorption means is a heating structure and is installed to partition the flow path, and
   each of the adsorbents includes an adsorption material coated on a surface of the heating structure.

4. The low-concentration air pollutant selective detection device of claim 3, wherein the heating structure is any one metal of iron (Fe), chromium (Cr), aluminum (Al), nickel (Ni), platinum (Pt), molybdenum (Mo), tungsten (W), and tantalum (Ta) or an alloy thereof.

5. The low-concentration air pollutant selective detection device of claim 4, wherein a plurality of concentrator parts are connected in parallel to each other in a main flow path.

6. The low-concentration air pollutant selective detection device of claim 3, wherein the heating structure is any one of silicon carbide (SiC)-based, molybdenum silicide (MoSi$_2$)-based, carbon-based, and zirconia-based heating elements.

7. The low-concentration air pollutant selective detection device of claim 3, wherein the adsorption material is any one or two or more selected from the group consisting of silica gel, activated alumina, synthetic zeolite, charcoal, bone charcoal, activated carbon, metal organic frameworks (MOF), hypercrosslinked polymeric resin (HPR), and zeolites.

8. The low-concentration air pollutant selective detection device of claim 1, further comprising:
   a main line which forms a main flow path through which the gas introduced from the outside moves to the sensor;
   the at least one concentrator part which is located in the main flow path; and
   a subline which is positioned between the at least one concentrator part and the sensor and forms a sub-flow path branched from the main flow path.

9. A method for selectively detecting the low-concentration air pollutant by using the device of claim 1, comprising:
   an adsorption mode including a step of adsorbing the different contaminants included in the gas, respectively, to the at least two adsorbents formed of the different materials; and
   a desorption mode including a step of individually detaching the different contaminants from the at least two adsorbents and moving the different contaminants to the sensor by using the desorption means positioned adjacent to each of the adsorbents,
   wherein the adsorption mode and the desorption mode are selectively performed.

10. The low-concentration air pollutant selective detection method of claim 9, wherein the adsorption mode includes a step in which a main flow path is opened and the gas is introduced into the at least one concentrator part located in the main flow path; a step of adsorbing the different contaminants to each of the adsorbents, and a step in which the gas passing through each of the adsorbents is discharged through a sub-flow path branched from the main flow path, and
   the desorption mode includes a step of desorbing the contaminants from each of the adsorbents by using the desorption means, a step of moving the desorbed contaminants to the sensor along the main flow path, and a step of measuring information including a concentration of the contaminants by the sensor.

11. The low-concentration air pollutant selective detection method of claim 9, wherein the desorption mode proceeds when a set period of time elapses in the adsorption mode.

* * * * *